US009265468B2

(12) United States Patent
Rai et al.

(10) Patent No.: US 9,265,468 B2
(45) Date of Patent: Feb. 23, 2016

(54) FLUOROSCOPY-BASED SURGICAL DEVICE TRACKING METHOD

(75) Inventors: Lav Rai, State College, PA (US); Jason David Gibbs, State College, PA (US); Henky Wibowo, Cupertino, CA (US)

(73) Assignee: BRONCUS MEDICAL, INC., Mountain View, CA (US)

( * ) Notice: Subject to any disclaimer, the term of this patent is extended or adjusted under 35 U.S.C. 154(b) by 631 days.

(21) Appl. No.: 13/105,710

(22) Filed: May 11, 2011

(65) Prior Publication Data

US 2012/0289825 A1 Nov. 15, 2012

(51) Int. Cl.
| | |
|---|---|
| A61B 6/00 | (2006.01) |
| A61B 6/12 | (2006.01) |
| A61B 19/00 | (2006.01) |
| A61B 6/03 | (2006.01) |

(52) U.S. Cl.
CPC . *A61B 6/12* (2013.01); *A61B 6/463* (2013.01); *A61B 6/466* (2013.01); *A61B 6/487* (2013.01); *A61B 6/50* (2013.01); *A61B 6/5235* (2013.01); *A61B 6/5247* (2013.01); *A61B 6/547* (2013.01); *A61B 19/5244* (2013.01); *A61B 6/032* (2013.01); *A61B 6/4441* (2013.01); *A61B 6/469* (2013.01); *A61B 6/582* (2013.01); *A61B 2019/5255* (2013.01); *A61B 2019/5291* (2013.01)

(58) Field of Classification Search
CPC ............ A61B 19/5244; A61B 2019/5255; A61B 2019/5291; A61B 6/032; A61B 6/12; A61B 6/4441; A61B 6/463; A61B 6/466; A61B 6/469; A61B 6/487; A61B 6/50; A61B 6/5235; A61B 6/5247; A61B 6/547
See application file for complete search history.

(56) References Cited

U.S. PATENT DOCUMENTS

| | | |
|---|---|---|
| 5,951,475 A | 9/1999 | Gueziec et al. |
| 6,351,513 B1 | 2/2002 | Bani-Hashemi |
| 6,580,938 B1 * | 6/2003 | Acker ........................... 600/424 |
| 6,614,453 B1 | 9/2003 | Suri et al. |
| 6,628,977 B2 | 9/2003 | Grauumann |
| 6,892,090 B2 | 5/2005 | Verard et al. |
| 6,920,347 B2 | 7/2005 | Simon et al. |
| 7,010,080 B2 | 3/2006 | Mitschke et al. |
| 7,035,371 B2 | 4/2006 | Boese et al. |
| 7,194,295 B2 | 3/2007 | Vilsmeier |
| 7,251,522 B2 | 7/2007 | Essenreiter |

(Continued)

OTHER PUBLICATIONS

P.M.Tate, V.Lachine, L.Fu, H.Croitoru and M.Sati, "Performance and Robustness of Automatic Fluoroscopic Image Calibration in a New Computer Assisted Surgery System," W.Niessen and M.Viergever (Eds.): MICCAI 2001, LNCS 2208, pp. 1130-1136, 2001.

(Continued)

*Primary Examiner* — Ruth S Smith
(74) *Attorney, Agent, or Firm* — Convergent Law Group LLP; Rick Batt (57) ABSTRACT

A method for assisting a physician track a surgical device in a body organ of a subject during a procedure includes fluoroscopic based registration, and tracking. An initial registration step includes receiving a 3D image data of a subject in a first body position, receiving a real time fluoroscopy image data, and estimating a deformation model or field to match points in the real time fluoro image with a corresponding point in the 3D model. A tracking step includes computing the 3D location of the surgical device based on a reference mark present on the surgical device, and displaying the surgical device and the 3D model of the body organ in a fused arrangement.

29 Claims, 6 Drawing Sheets

(56) References Cited

U.S. PATENT DOCUMENTS

| | | |
|---|---|---|
| 7,398,116 B2 | 7/2008 | Edwards |
| 7,508,388 B2 | 3/2009 | Barfuss et al. |
| 7,508,392 B2 | 3/2009 | Barfuss et al. |
| 7,508,913 B2 | 3/2009 | Boese et al. |
| 7,555,331 B2 | 6/2009 | Viswanathan |
| 7,590,442 B2 | 9/2009 | Boese et al. |
| 7,599,730 B2 | 10/2009 | Hunter et al. |
| 7,689,019 B2 | 3/2010 | Boese et al. |
| 7,689,042 B2 | 3/2010 | Brunner et al. |
| 7,756,308 B2 | 7/2010 | Viswanathan |
| 7,756,563 B2 | 7/2010 | Higgins |
| 7,764,984 B2 | 7/2010 | Desmedt et al. |
| 7,787,932 B2 | 8/2010 | Vilsmeier et al. |
| 7,801,342 B2 | 9/2010 | Boese et al. |
| 7,853,305 B2 | 12/2010 | Simon et al. |
| 7,853,307 B2 | 12/2010 | Edwards et al. |
| 7,853,308 B2 | 12/2010 | Sauer et al. |
| 7,889,905 B2 | 2/2011 | Higgins |
| 2003/0073901 A1 | 4/2003 | Simon et al. |
| 2003/0088179 A1 | 5/2003 | Seeley et al. |
| 2003/0181809 A1 | 9/2003 | Hall et al. |
| 2005/0119561 A1 | 6/2005 | Kienzle, III |
| 2006/0079759 A1* | 4/2006 | Vaillant et al. ............... 600/424 |
| 2008/0183073 A1 | 7/2008 | Higgins |
| 2008/0262342 A1 | 10/2008 | Averbuch |
| 2009/0105579 A1 | 4/2009 | Garibaldi |
| 2009/0163800 A1 | 6/2009 | Xu |
| 2010/0030064 A1 | 2/2010 | Averbuch |
| 2010/0049038 A1 | 2/2010 | Florent et al. |
| 2010/0228117 A1* | 9/2010 | Hartmann ..................... 600/424 |
| 2010/0292565 A1 | 11/2010 | Meyer et al. |
| 2011/0054309 A1 | 3/2011 | Edwards |
| 2011/0091087 A1* | 4/2011 | Ibarz et al. ................... 382/131 |
| 2011/0295111 A1* | 12/2011 | Hansis et al. ................ 600/424 |
| 2012/0294498 A1* | 11/2012 | Popovic ....................... 382/128 |
| 2013/0094742 A1* | 4/2013 | Feilkas ......................... 382/131 |

OTHER PUBLICATIONS

Z.Zhang, "Flexible camera calibration by viewing a plane from unknown orientations," ICCV1999, pp. 666-673.

L.Zollei, "2D-3D Rigid-Body Registration of X-Ray Fluoroscopy and CT Images," Massachusetts Institute of Technology, Aug. 2001.

PCT International Search Report and Written Opinion of the International Searching Authority, issued Nov. 16, 2012, Application No. PCT/US2012/037026.

Knecht et al., "Computed Tomography-Fluoroscopy Overlay Evaluation During Catheter Ablation of Left Atrial Arrhythmia", Europace Advance Access, published May 28, 2008.

PCT/US2012/037026, International Preliminary Report on Patentability, Nov. 21, 2013, The International Bureau of WIPO.

M.M.Coselmon, J.M.Balter, D.L.McShan and M.L.Kessler, "Mutual information based CT registration of the lung at exhale and inhale breathing states using thin-plate splines," American Association of Physicists in Medicine, Oct. 2004.

R.Fahrig, M.Moreau and D.W.Holdsworth, "Three-dimensional computed tomographic reconstruction using a C-arm mounted XRII: Correction of image intensifier distortion," 1997 American Association of Physicists in Medicine, Apr. 1997.

R.Fahrig, M.Moreau and D.W.Holdsworth, "Three-dimensional computed tomographic reconstruction using a C-arm mounted XRII: Image-based correction of gantry motion nonidealities," 2000 American Association of Physicists in Medicine, Oct. 1999.

D.A.Forsyth and Jean Ponce, "Computer Vision: A modern approach," Prentice Hall Professional Technical Reference, 2002.

A.Gueziec and P.Kazanzides, "Anatomy-Based Registration of CT-Scan and Intraoperative X-Ray Images for Guiding a Surgical Robot," IEEE Transactions on Medical Imaging, vol. 17, No. 5, Oct. 1998.

L.F.Gutierrez, C.Ozturk, E.R.McVeigh and R.J.Lederman, "A practical global distortion method for an image intensifier based x-ray fluoroscopy system," MedPhys. Mar. 2008, pp. 997-1007.

J.Heikkila and O.Silven, "A four-step camera calibration procedure with implicit image correction," CVPR 1997, pp. 1106-1112.

R.Hofstetter, M.Slomczykowski, M.Sati and L.P.Nolte, "Fluoroscopy as an Imaging Means for Computer-Assisted Surgical Navigation," Computer Aided Surgery, 4:65-76, 1999.

T.Leloup, W. El Kazzi, O.Debeir, F.Schuind and N.Warzee, "Automatic fluoroscopic image calibration for traumatology intervention guidance," Eurocon2005, pp. 374-377.

A.K.Jain, T.Mustafa, Y.Zhou, C.Burdette, G.S.Chirikjian and G.Fichtinger, "FTRAC—A robust fluoroscope tracking fiducial," Med.Phys. 32, Oct. 2005.

S.Jonic, P.Thevenaz, G.Zheng, L.P.Nolte and M.Unser, "An Optimized Spline-Based Registration of a 3D CT to a Set of C-Arm Images," International Journal of Biomedical Imaging, vol. 2006, Feb. 2006, pp. 1-12.

L.Joskowicz, D.Knaan, H.Livyatan, Z.Yaniv, A.Khoury, R.Mosheiff and M.Liebergall, "Anatomical image-based rigid registration between fluoroscopic X-ray and CT: methods comparison and experimental results," School of Computer Science and Eng., Hebrew Univ. of Jerusalem, Israel, Orthapedic Surgery Dept., The Hadassah-Hebrew Univ. Medical School, Israel, pp. 1-5.

D.A.LaRose, Iterative X-Ray/CT Registration Using Accelerated Volume Rendering, Carnegie-Mellon University, May 2001.

H.Livyatan, Z.Yaniv and L.Joskowicz, "Gradient-Based 2-D/3-D Rigid Registration of Fluoroscopic X-Ray to CT," IEEE Transactions on Medical Imaging, vol. 22, No. 11, Nov. 2003.

Ph.Merloz, J.Troccaz, H. Vouaillat, Ch.Vasile, J.Tonetti, A.Eid and S.Plaweski, "Fluoroscopy-based Navigation system in Orthopaedic Surgery," University Department of Orthopaedic and Trauma Surgery; CHU A. Michallon ; BP 217, 38043 Grenoble cedex 09 France, Equipe GMCAO—Laboratoire TIMC/IMAG (Université Joseph Fourier—CNRS).

P.Muyan-Ozcelik, J.D.Owens, J.Xia and S.S.Samant, "Fast Deformable Registration on the GPU: A CUDA Implementation of Demons," Proceedings of the 2008 International Conference on Computational Science and Its Applications (ICCSA), IEEE Computer Society Press, Jun. 2008.

D.Rueckert, L.I.Sonoda, C.Hayes, D.L.G.Hill, M.O.Leach and D.J. Hawkes, "Nonrigid Registration Using Free-Form Deformations: Application to Breast MR Images," IEEE Transactions on Medical Imaging, vol. 18, No. 8, Aug. 1999.

Y.Sakai, Y.Matsuyama, H.Yoshihara, H.Nakamura, S.Nakashima and N.Ishiguro, "Simultaneous Registration with CTFluoro Matching for Spinal Navigation Surgery," Nagoya J. Med. Sci, 68, pp. 45-52, 2006.

Extended European Search Report dated Oct. 24, 2014 for European Application No. EP12781811.0 from PCT/US2012/037026.

* cited by examiner

FLUOROSCOPY-BASED SURGICAL DEVICE TRACKING METHOD

CROSS-REFERENCE TO RELATED APPLICATIONS

None

FIELD OF THE INVENTION

The present invention relates to surgical procedures and in particular, to assisting physicians with tracking and guidance during surgical procedures.

BACKGROUND OF THE INVENTION

Minimally invasive surgery is surgery performed with only a small incision or no incision at all and is typically performed with an endoscope, bronchoscope, laparoscope, or like instrument.

In a bronchoscopic procedure, for example, a bronchoscope is inserted through the nose or mouth of the patient, advanced through the trachea and into a desired airway. The surgery may then be performed through the working lumen of the bronchoscope. A light source and camera at the tip of the bronchoscope enables the physician to observe the airway wall in real time. A skilled physician can identify his location along the airway and navigate to the desired location along the airway wall.

It is often desirable, however, to supplement endoscopic visualization with radiological guidance (e.g., by taking real time X-ray images of the region with a fluoroscope). In certain procedures radiologic guidance is necessary.

In a transbronchial needle aspiration (TBNA) procedure, for example, a long flexible catheter comprising a needle at the tip is advanced through the working lumen of the bronchoscope to the target site. The needle is then advanced through the airway wall outside of view of the bronchoscope to aspirate a sample of tissue. It is highly desirable or necessary to have fluoroscopy or an alternative means to view and track the needle once it is outside of view of the bronchoscope.

Tracking devices using a fluoroscope, however, is not straightforward. To track a device, multiple 2D X-ray images from multiple different fluoroscopic camera views are taken. Based on the information provided by these two images, the physician determines the position of the device. Determining the position based on two 2D X-rays relies on the skill and experience of the physician. Even for the most skilled physicians there is a considerable degree of uncertainty. This is undesirable.

One approach to address the above mentioned problem is described in US Patent Publication No. 2003/0181809 to Hall et al. (hereinafter referred to as "the Hall Publication"). The Hall Publication describes a method of visualizing a surgical instrument that has been introduced into an area of examination within a patient, in particular a catheter that is used during a cardiological examination or treatment, comprising the following steps: using a 3D image data set of the area of examination and generating a 3D reconstructed image of the area of examination, taking at least one 2D X-ray image of the area of examination in which the instrument is visualized, registering the 3D reconstructed image relative to the 2D X-ray image, and visualizing the 3D reconstructed image and superimposing the 2D X-ray image over the 3D reconstructed image on a monitor.

Although the Hall Publication addresses visualization of the heart and central vasculature tree using a rigid registration technique, and compensates for the rhythmatic motion of the heart, the Hall Publication does not appear to address body organ applications in which the shape and position of the body organ is affected by the position or posture of the patient. In such unfixed or non-rigid body organ applications, it is difficult to visualize the non-rigid body organs because the position (or posture) of the patient's body during the pre-operative image scans may be substantially different than his position during the surgical procedure. Although this is of no consequence for certain organs that are generally rigid in one body position or another such as the heart, spine and brain, a change in patient position for non-rigid body organs presents a challenge because previously acquired 3D image data and the 3D model arising there from will not match the real-time image organ data. In addition to the difference in posture/position of the patient, the "static" pre-operative scans may also differ from the real-time "moving" images due to the motion induced by breathing. Stated another way, the shape of the organ from the pre-operative scans shall not match the shape of the organ during the procedure. This thwarts live tracking and guidance.

A method and system to assist surgeons to track surgical devices in a body organ, that has application to non-rigid organs such as the lung, and that does not suffer the above identified drawbacks is therefore desired.

SUMMARY OF THE INVENTION

One embodiment of the present invention is a method for tracking a surgical device in a non-rigid body organ of a subject in real time. The method includes receiving at least one 3D image or 3D image data set of the non-rigid body organ in a first position and computing a 3D model of the body organ; receiving fluoroscopy images from one or more views in real-time from a fluoroscopy unit of the body organ and showing at least one reference mark in the non-rigid body organ along with the surgical device; and deforming the 3D model of the non-rigid body organ to match the body organ of the subject in a second position based on at least one reference mark. The reference marks may include anatomical features such as the spine, ribs, etc. or device-based features such as a pattern on the device, the tip of the device at known anatomical landmarks, fiducial markers, etc. The method may further include applying the deformation field to register the fluoroscopy images with the 3D model. The registration determines the fluoroscopic camera locations corresponding to fluoroscopic images. Multiple views of the surgical device in fluoroscopic images then give its 3D location in the 3D image.

In another embodiment of the present invention, the method further comprises the step of sending to a display at least one information for display fused with the 3D image and also fused with the 2D fluoroscopic images. The information may include a) the 3D location of the surgical device; b) a region of interest (ROI); or c) a virtual path to the ROI.

In another embodiment of the present invention, the non-rigid body organ is the lung and the ROI is outside of an airway tree.

In another embodiment of the present invention, the method applies a video-based registration and guidance algorithm when the surgical device is within the airway and applies a fluoro-based registration algorithm when the surgical device is outside of the airway. In particular, the method further includes a step of receiving a real-time endoscopic image of an airway while the surgical device is within the airway, and registering the real-time endoscopic image with the 3D image of the non-rigid body organ.

In another embodiment of the present invention a method for tracking a surgical device in a body organ of a subject during a surgical procedure, and guiding the surgical device to a ROI in the body organ includes: receiving at least one 3D image of the body organ and computing a 3D model of the body organ; receiving a real-time fluoroscopy image from a fluoroscopy unit wherein the fluoroscopy image shows a reference mark of the surgical device at a tracking location; registering the 3D image with the real-time fluoroscopy image; and computing a 3D location of the surgical device in the 3D model based on characteristics of the reference mark.

In another embodiment of the present invention, a surgical device includes a reference mark which is visible under fluoroscopy. In one embodiment the reference mark is a plurality of bands. In another embodiment the mark is cross shaped. In another embodiment, a system includes a workstation operable to track a surgical device using a fluoroscopy based registration algorithm and based on a reference mark on the surgical device. The system includes the surgical device. In one embodiment the surgical device is an endoscope or catheter.

In another embodiment of the present invention, a method for tracking a surgical device in a body organ of a subject during a surgical procedure, and guiding the surgical device to a region of interest (ROI) in the body organ, includes receiving a 3D image of the body organ and computing a 3D model of the body organ; receiving a real-time fluoroscopy image from a fluoroscopy unit wherein the fluoroscopy image shows the reference mark of the surgical device at a tracking location; registering the 3D image with the fluoroscopy image; and computing a 3D location of the surgical device in the 3D model based on at least one constraint, wherein the constraint includes limiting the body organ to that of an airway tree and requiring the reference mark to be inside a lumen of the airway tree.

In another embodiment of the present invention, the constraint includes assuming the device which carries the reference mark is substantially inside the lumen of the airway tree. The system computes the position and orientation of the device in 3D space based on this constraint. The orientation of the device as it leaves the airway tree and travels through lung tissue may be estimated or predicted.

In another embodiment of the present invention a method for tracking a surgical device in a body organ of a subject during a surgical procedure, and guiding the surgical device to a region of interest (ROI) in the body organ includes the steps of: receiving a plurality of non-continuous discrete fluoroscopy images from a fluoroscopy unit while the reference mark is at a tracking location and each of the plurality of fluoroscopy images showing the reference mark of the device in the body organ and computing the 2D location of the reference mark in each of the plurality of fluoroscopy images. The method additionally includes the step of computing the 3D location of the reference mark in a 3D model of the body organ, wherein the computing step is based on determining an intersection of a ray extending from the fluoroscopy unit, to the reference mark of the device in each of the plurality of fluoroscopy images.

In another embodiment of the present invention a system is provided which includes a workstation. The workstation may be a portable computer or laptop. The workstation includes a processor operable to receive a 3D image of the non-rigid body organ in a first position and computing a 3D model of the body organ; to receive a real-time fluoroscopy image from a fluoroscopy unit of the body organ and showing a reference mark in the non-rigid body organ; and to deform the 3D model of the non-rigid body organ to match the body organ of the subject in a second position and based on the reference mark. In one embodiment the reference mark is part of the surgical device enabling tracking of the surgical device through the body organ in real time based on the reference mark. In another embodiment the workstation is operable to estimate a deforming field or deformation model of the 3D model for matching any point of the real time fluoroscopy image to a point in the body organ. In another embodiment the system further includes a display for presenting the surgical device in combination or fused with the 3D model. In another embodiment the system further comprises a catheter or instrument which includes a reference mark for facilitating fluoroscopy based tracking during a real time procedure.

The description, objects and advantages of the present invention will become apparent from the detailed description to follow, together with the accompanying drawings.

DETAILED DESCRIPTION OF THE INVENTION

Before the present invention is described in detail, it is to be understood that this invention is not limited to particular variations set forth herein as various changes or modifications may be made to the invention described and equivalents may be substituted without departing from the spirit and scope of the invention. As will be apparent to those of skill in the art upon reading this disclosure, each of the individual embodiments described and illustrated herein has discrete components and features which may be readily separated from or combined with the features of any of the other several embodiments without departing from the scope or spirit of the present invention. In addition, many modifications may be made to adapt a particular situation, material, composition of matter, process, process act(s) or step(s) to the objective(s), spirit or scope of the present invention. All such modifications are intended to be within the scope of the claims made herein.

Methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail).

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. It is to be appreciated that unless defined otherwise, all technical and scientific terms used herein have the same meaning as commonly understood by one of ordinary skill in the art to which this invention belongs.

Figure 1:
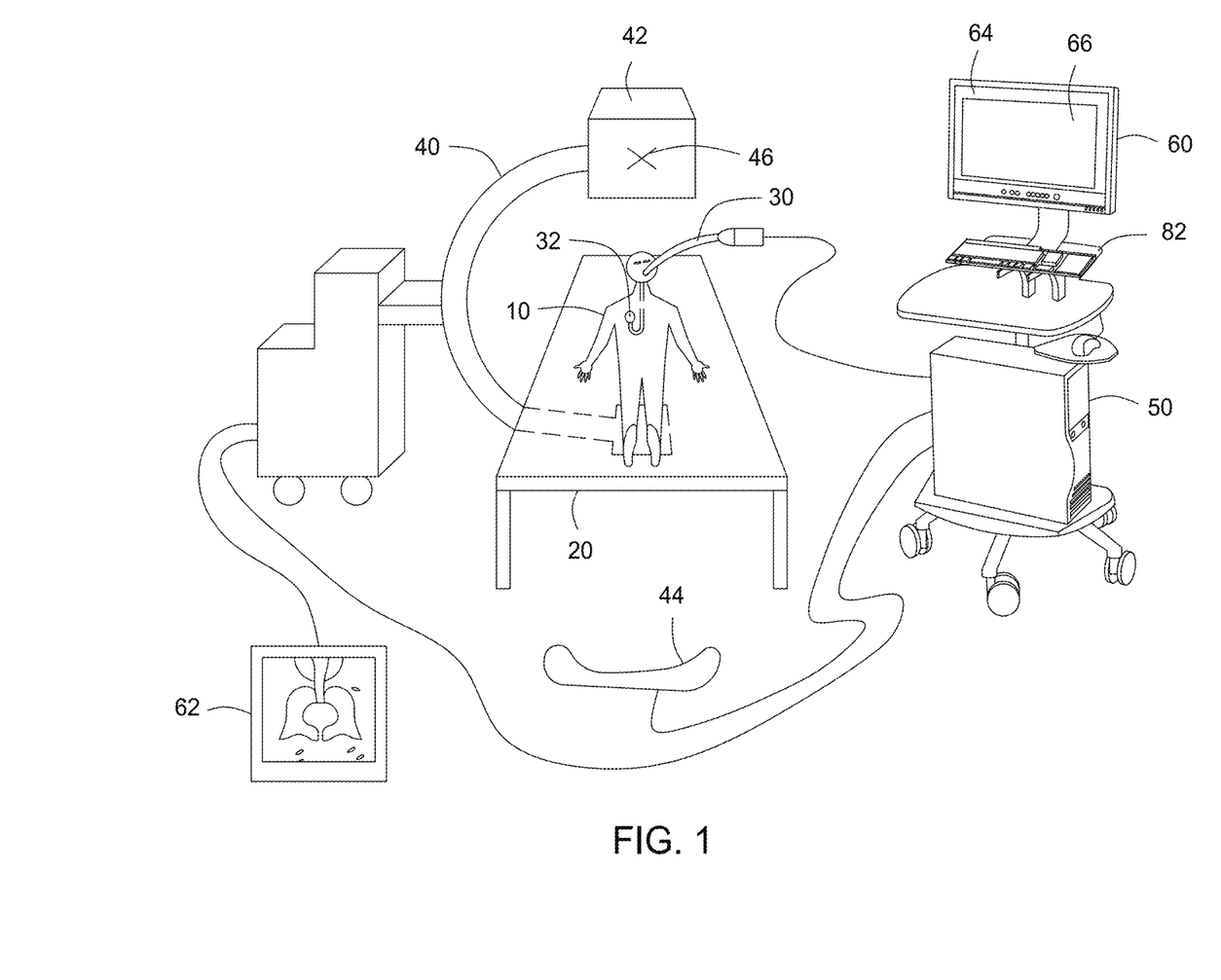
FIG. 1 is a schematic diagram of a subject on a table during a surgical procedure.

FIG. 1 illustrates a schematic diagram of a surgical setting in an operating room including a workstation 50 in accordance with the present invention. In particular, FIG. 1 illustrates a subject 10 on an operating table 20. Although the subject shown in FIG. 1 is a human, the invention is applicable to animals other than humans and may be performed on live or dead animals or subjects as the case may be.

With reference to FIG. 1, a surgical device 30 is shown positioned and extending into a lung of the subject. The surgical device 30 has a distal working end or tip 32 which has been passed through the subject's mouth, the trachea, a bronchi, and into the lung. While surgical device 30 shown in FIG. 1 is intended to represent an endoscope, namely, a bronchoscope, the invention is not so limited. The surgical device may be a wide range of devices, instruments, implants, and markers which are visible under fluoroscopy, have a portion which is visible under fluoroscopy, or be modifiable such that it is visible under fluoroscopy. Examples, without limitation, include catheters, sheaths, needles, ablation devices, stents, valves, fiducial markers, seeds, coils, etc.

A fluoroscope 40 takes real time fluoroscopic video of the subject. Video frames of the video or images are collected or received by workstation 50 for processing. Real time images may also be displayed on a video monitor 62. The location and pose of the fluoroscopy camera 42 is tracked with a tracking sensor 44. In the fluoroscopy unit shown in FIG. 1, an optically visible symbol 46 is observed by the optical tracking sensor 44 to provide to workstation 50 information about the location, orientation and pose of the fluoroscopy camera 42 in real time. The optical tracking sensor 44 may be positioned on any fixed surface including the floor, wall, ceiling, or a table. Although the tracking sensor shown in this embodiment is optically based, other techniques (for example, electromagnetic) to track the camera may be employed and are in accordance with the present invention. Moreover, the fluoroscopic camera may be tracked without using any sensor. This can be done by image-based tracking where reference markers with known 3D geometry are viewed by the fluoroscopic camera. The images of the reference markers give 2D points which can then be used by a 3D-2D pose estimation algorithm to estimate the fluoroscopic camera location. A 3D-2D pose estimation algorithm is described in Reference 1.

Workstation 50, as will be described in more detail below, is configured to receive the fluoroscopy images from the fluoroscopy unit 40 in real-time and to compute the 3D location of the surgical device or as the case may be, the end 32 of the surgical device.

FIG. 1 also illustrates a display 60 showing a plurality of images. As will be described in greater detail herein, workstation 50 is configured to send to the display a number of types of images including 3D model views, 2D model fluoroscopy views, real fluoroscopy views, real endoscopic views, model endoscopic views, and a wide range of information superimposed on the views such as without limitation planning information, region of interests, virtual target markers, vessels, virtual obstacles, real devices, virtual devices, routes to a target, notes and indicia provided by the user, etc.

The workstation 50 shown in FIG. 1 registers the observed location of the surgical device shown in the fluoroscopy images from the fluoroscope unit 40 with the 3D location in a 3D model of the subject. As described herein, the information and location may be displayed in a number of ways to the physician to assist tracking the surgical device in real time, and in the event planning information has been provided to the workstation, to guide the physician to a target. Various planning information may be provided or determined by the workstation as described in U.S. Patent Application No. 2008/0183073 to Higgins et al., for example.

Figure 2:
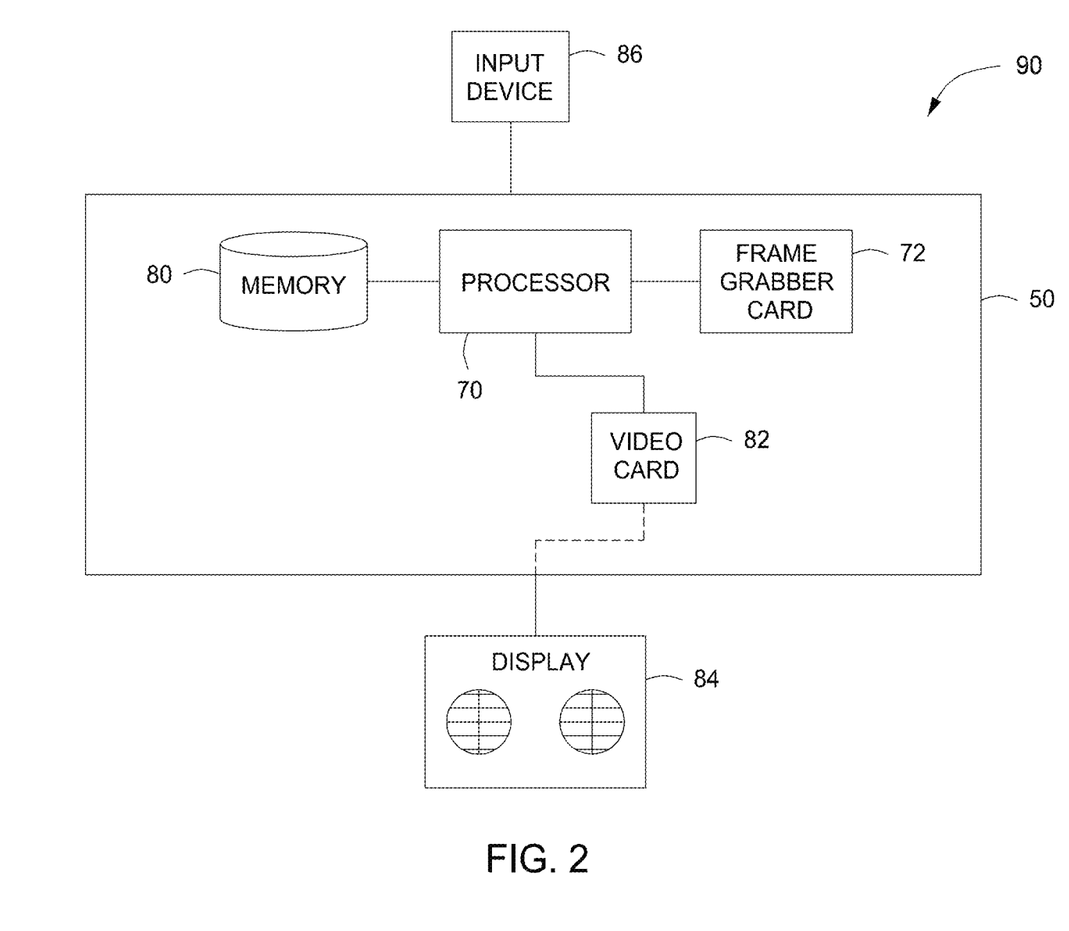
FIG. 2 is a block diagram of a surgical tracking system in accordance with one embodiment of the present invention.

FIG. 2 illustrates a surgical device tracking system 90 including a workstation or specially programmed computer 50. The workstation 50 shown in FIG. 2 includes a processor 70 operable to determine the 3D location of the surgical device in real time based on, amongst other things, the real-time fluoroscopy images as will be described in more detail herein.

Workstation 50 is also shown having a memory device 80 which holds or stores information including imaging, device, marker, and procedural data. The memory device may be hard drive, for example.

The workstation 50 shown in FIG. 2 is adapted to receive real-time images (e.g., fluoroscopy or endoscopy images) through various input ports or connectors (e.g., USB port, video port, etc.). A frame grabber card 72 is present to capture individual video frames or images for processing. Real time fluoroscopy images may be obtained by the workstation 50, for example, from continuous fluoroscopy video, video clips, and/or still frames. The workstation is further adapted to send image data to a display using a video card 82. An example of a workstation is a Dell Computer Model No. T5400, with Dual-core Intel Xeon 2.0 GHz processor, and a Nvidia Quadro FX 3800 video card.

The system 90 shown in FIG. 2 also includes a display 84 which may present reports, data, images, results and models in various formats including without limitation graphical, tabular, and pictorial form. In one embodiment of the present invention, a surgical device is superimposed on a 3D model of the organ.

It is to be understood, however, that although the system in FIG. 2 is shown with a memory 80 for receiving and storing various information the invention is not so limited. In an alternative embodiment the system may be configured to merely access a memory device such as a USB stick, a CD, or other media storage device.

The system 90 shown in FIG. 2 also includes a user input device 86 such as, for example, a keyboard, joystick, or mouse. The user input device allows a user such as the physician to add or input data and information as well as modify planning information and to make notes in the files and records.

In another embodiment the processor is connectable to a memory device through the internet or through another communication line to access a network. For example, patient data CT scans may be stored on a server of a hospital and the processor of the instant application is adapted to access such data via a communication line and process the data.

The displays may be incorporated with the processor in an integrated system (e.g., a lap top, or larger pad-type computer) or the displays may cooperate with the processor from a remote location. A processor may be adapted to send or deliver data across a network to one or more displays, tablet computers, or portable computer devices or smart phones such as the Iphone® manufactured by Apple, Inc. Cupertino, Calif., United States. Indeed, although the computer system 90 shown in FIG. 2 includes a number of various components incorporated into a system, the invention is not so limited. The invention is intended to be limited only as defined in the appended claims.

Figure 3:
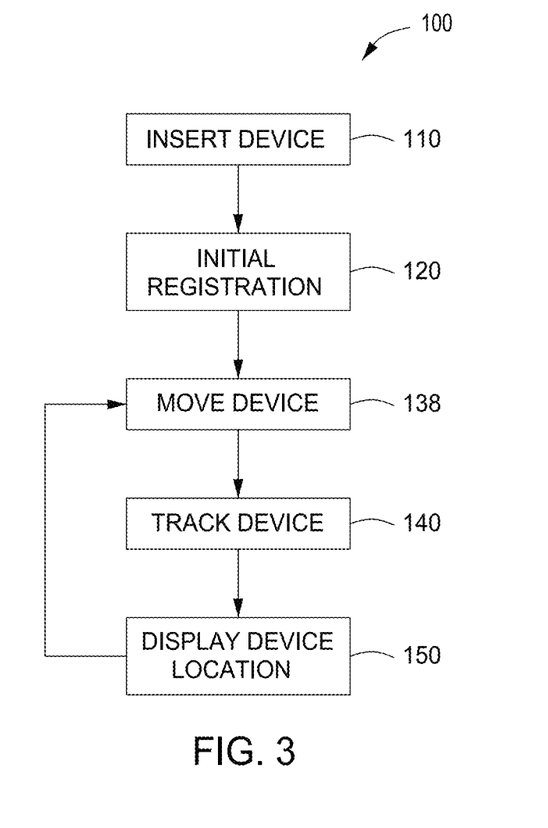
FIG. 3 is a flow chart of a surgical procedure for tracking a surgical device.

FIG. 3 is a flow chart illustrating an overview of a surgical procedure 100 for tracking a surgical device and displaying information about the surgical device in real time. First, step 110 insert a surgical device into the body organ. As indicated above, the surgical device may vary widely and include, for example, an endoscope or bronchoscope, a treatment device such as an ablation catheter, sheath, forceps, brush, or biopsy needle, an implant such as a stent, valve, coil, or fiducial marker. Next, step 120 initially registers 3D model data of the body organ with real-time fluoroscopy data generated by a fluoroscope prior to moving the device. This step is done to register the initial pose of the fluoroscope camera with 3D model.

Although not shown in the figure, a fluoroscopic-camera calibration step may be performed prior to the registration step and used as an input to the registration step. Calibration data may be obtained off-line and be calculated by acquiring multiple fluoroscopic images of radio-opaque markers to determine such data as the focal lengths and camera center of fluoroscopic camera, and a representation of the deformation pattern wherein a checkerboard pattern appears curved when viewed in the fluoroscope, and variation of these parameters as the fluoroscope is rotated throughout its range of motion. The calibration factors can be specific to each fluoroscope. Examples of calibrating techniques include those described in Z. Zhang, "Flexible camera calibration by viewing a plane from unknown orientations", ICCV1999, pages 666-673; J. Heikkila and O. Silven, "A four-step camera calibration procedure with implicit image correction", CVPR1997, pages 1106-1112; T. Leloup, W. El Kazzi, O. Debeir, F. Schuind, and N. Warzee, "Automatic fluoroscopic Image Calibration for traumatology intervention guidance", Eurocon2005, pages 374-377; L. F. Gutierrez, C. Ozturk, E. R. McVeigh, and R. J. Lederman, "A practical global distortion correction method for an image intensifier based x-ray fluoroscopy system" Medical Physics March 2008, 35(3), pages 997-1007. The camera calibration step may be incorporated into the method and system of the present invention and performed prior to the initial registration step, and used as an input for the initial registration as well as for registration during continuous tracking.

Next, step 138 moves the surgical device. For example, a physician may advance the surgical device through an airway wall of the lung into the parenchyma. The fluoroscopic camera may also be moved to get another view of the device.

Next, step 140 tracks the location the device. As the surgical device is moved, this step tracks the device, namely, computes the location of the surgical device in the 3D model. This step 140 shall be described in greater detail with reference to FIG. 5.

Finally, method 100 shows step 150 displaying the device location. Displaying the device location provides tracking and guidance information to the user or physician. In one embodiment, a virtual surgical device is superimposed onto a 3D view of the body organ. Additionally, because the 3D location of the surgical device is computed from step 140, the surgical device may be superimposed on model projection 2D fluoroscopy view. Indeed, a number of views showing the surgical device, as well as any additional markers, routes, indicia and planning information may be displayed with model or real images of the organ. Another surgical-guidance method may be provided without executing step 140. Instead of estimating location of surgical device, only the "planned" location of the surgical device and ROI is projected and superimposed on 2D fluoroscopy view. The physician may then visually compare the "planned" projection and actual image of the surgical device to navigate to the ROI.

Figure 4:
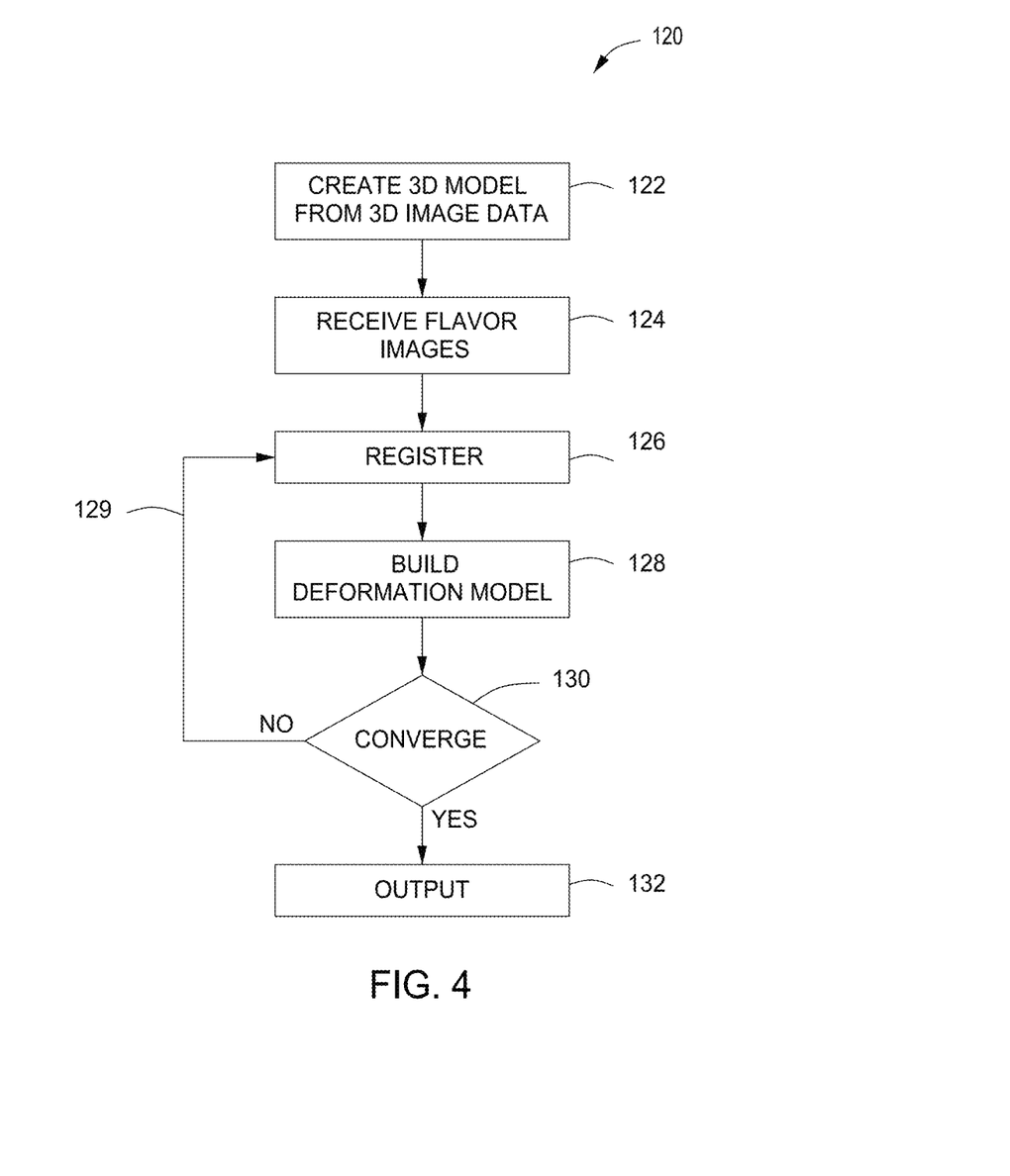
FIG. 4 is a flow chart of a surgical procedure for estimating or building a deformation model based on previously acquired 3D image data and fluoroscopy images.

FIG. 4 is flow chart diagram illustrating a registration method 120 in accordance with the present invention for assisting a physician to track a surgical device during a live procedure. The steps may be carried out on a computer or system and include: step 122 creating a 3D model of a body organ; step 124 receiving at least one real-time fluoroscopy image of the body organ; 126 registering a 3D point from the model to a 2D fluoroscopy point in the at least one fluoroscopy image; and step 128 deforming the 3D model of the body organ to match the real-time organ.

The step 122 of creating a 3D model of a body organ, in one embodiment, includes creating a 3D model of a non-rigid body organ such as the lung in a first body position or first patient position. The 3D model of the body organ is created from input including available image data from the subject such as, for example, high resolution computed tomography (HRCT) scans. Other acceptable data sets include without limitation MRI, PET, 3D angiographic, and X-ray data sets. In a method, or system, the workstation receives a 3D image file, 3D image data set, or a set of 2D images of the organ from which a 3D model of the organ may be computed. The workstation may communicate with the DICOM, for example, to receive such data sets. An exemplary technique to determine a 3D model of the body organ is disclosed in U.S. Pat. No. 7,756,316 entitled "Method and system for automatic lung segmentation". See also, U.S. Pat. Nos. 7,889,905 and 7,756,563; and Patent Publication No. 2008/0183073 all to Higgins et al.

Next, step 124 recites receiving fluoroscopy images of the subject. Real-time fluoroscopy images of the body organ are obtained while the subject is in a second position which may not be identical to the first position. For example, the patient may be curled, hyper extended, or otherwise in a different body posture on the operating table than during the pre-operative 3D scans. Certain organs, such as non-rigid body organs may be deformed due to the subject's body posture, patient orientation, inspiration level, and position. An example of a non-rigid body organ is the lung. Also, by "non-rigid body organ", it is meant to exclude the heart and other body organs that do not normally change shape as a result of varying patient body posture or position. Consequently, the 3D model of the subject in the first position may not match that of the subject in the second real-time position. The fluoroscopy images may also span a complete breathing cycle for a particular fluoroscope camera position.

Step 126 recites registering of the 3D image with a real time fluoroscopy image. Exemplary types of 3D-2D registration may be a) reference mark based b) intensity based or c) location-based. An example of both techniques is given by W. E. Higgins, S. A. Merritt, and L. Rai, "Guidance method based on 3D-2D pose estimation and 3D-CT registration with application to live bronchoscopy", U.S. Pat. No. 7,756,563 B2. W. E. Higgins, S. A. Merritt, and L. Rai, "Fast 3D-2D image registration method with application to continuously guided endoscopy", U.S. Pat. No. 7,889,905 gives another example of intensity-based registration. Additionally, the reference mark may vary widely. The reference mark may include, for example, a point corresponding to that of the body organ itself such as a point along an airway wall, ribs, spine, a ROI, or the point may correspond to a marker, catheter, implant, device, etc. inserted by a physician.

The intensity-based approach is a preferred embodiment for matching projection (virtual fluoroscopic image) for a given real-time fluoroscopic image. The matching criterion can be mutual-information, cross-correlation, etc. It should also be understood that step 126 provides for registering one point or multiple points. In this manner, a pattern or set of points corresponding to a target or marker, for example, may be registered.

Location based registration requires the user to go to a known location under fluoroscopy and registration is performed based on the known location or anatomical landmark. For example, the device may be moved to the main carina and the 3D model image is matched to the 2D fluoro image at this known location.

Registering step 126 may be additionally based on application of a 3D deformation model (step 128) to the 3D image. The 3D deformation model is desired because the 3D model of the subject in the first position may not match that of the subject in the second real-time position. The 3D deformation model may either be available before hand or is estimated by step 128. The 3D deformation model applied to the 3D image generates a modified set of 3D locations which are then used for registration.

In one embodiment a loop 129 between step 126 and step 128 is continued until a maximum estimated deformation in step 128 is less than a threshold value. This computation is shown in step 130 of FIG. 4. An example of a threshold value ranges from 0.5 and 5 mm and can be set to about 1 mm. Additionally, step 126 and step 128 can be performed separately or together as joint estimation of camera pose and deformation model.

An output of the method shown in FIG. 4 is depicted by step 132. The output may be the fluoroscopic camera orientation and location, (namely, the pose) corresponding to the real-time fluoroscopic image. Step 126 can use multiple fluoroscopic images for pose estimation as well. Step 128 may then refine the 3D deformation model estimate based on fluoroscopic camera pose.

A 3D deformation model may be refined such that any point in the fluoroscopy image may be matched with a point in the 3D model.

In one embodiment the 3D model of the body organ is deformed, and a 2D projection image from the 3D model is compared to that of the real time 2D fluoroscopy image. A 2D delta or difference between the image created from the 3D model and the real fluoroscopy image is calculated. This 2D difference gives a constraint on the 3D motion of the reference mark by using the fluoroscopic camera pose. More such constraints can be generated from multiple fluoroscopic images to give the 3D motion of the reference mark. This estimated 3D motion can then be propagated to neighboring 3D points using smoothness constraints or optical flow constraints. An example of optical flow constraint applied to deformation model is given by "Fast Deformable Registration on the GPU: A CUDA Implementation of Demons" by Pinar Muyan-Ozcelik, 2008. A warping algorithm for warping a live image with a model image is also disclosed in U.S. Pat. No. 7,889,905 to Higgins et al. A deformation model may be estimated as an output of the deformation step.

In one embodiment of the present invention, a time point relative to the breathing cycle of the subject at which time the real-time fluoroscopy image matches or best matches a fluoroscopy-projection of the 3D model may be estimated. The match can be image-based or reference-mark based as described herein. The time point estimation is based on identifying the point in time during the breathing motion profile at which the real-time fluoroscopy image matches the model image. An embodiment of the present invention therefore can provide image registration with the 3D model and also time information relative to the subject's breathing cycle. As the 3D model can be deformed to reflect a range of deformations throughout the breathing cycle, this embodiment can also provide registration through the entirety of the breathing cycle.

A breathing motion profile corresponding to the respiratory cycle of the patient may created from the CT data, or otherwise input to workstation. This may be input or received in the form of, for example, image data of the bronchial tree and airways at multiple points in time corresponding to inhalation, exhalation, and perhaps one or more time points between inspiration and expiration. The data may be processed to identify displacement of tissues and tissue surfaces. A review of the image data across multiple points in time serves to accurately show the breathing motion profile of the patient. An exemplary process for carrying this out is described in "Fast Deformable Registration on the GPU: A CUDA Implementation of Demons" by Pinar Muyan-Ozcelik, 2008 wherein the authors describe using a pair of CT scans acquired from the same patient, one at a full level of inspiration and the second at a full level of expiration. The deformable registration technique described in this paper gives the mapping of each discrete point within the lungs from its geometric location at expiration to inspiration and from inspiration to expiration. From these mappings, the location of any region within the chest can be estimated at points during the breathing cycle. See also the Hall Publication describing registration and compensating for the rhythmatic motion of the heart when performing registration. Multiple pairs of scans (e.g. Full inspiration and full expiration scans from more than one person) may also be used to create this data set.

Figure 5:
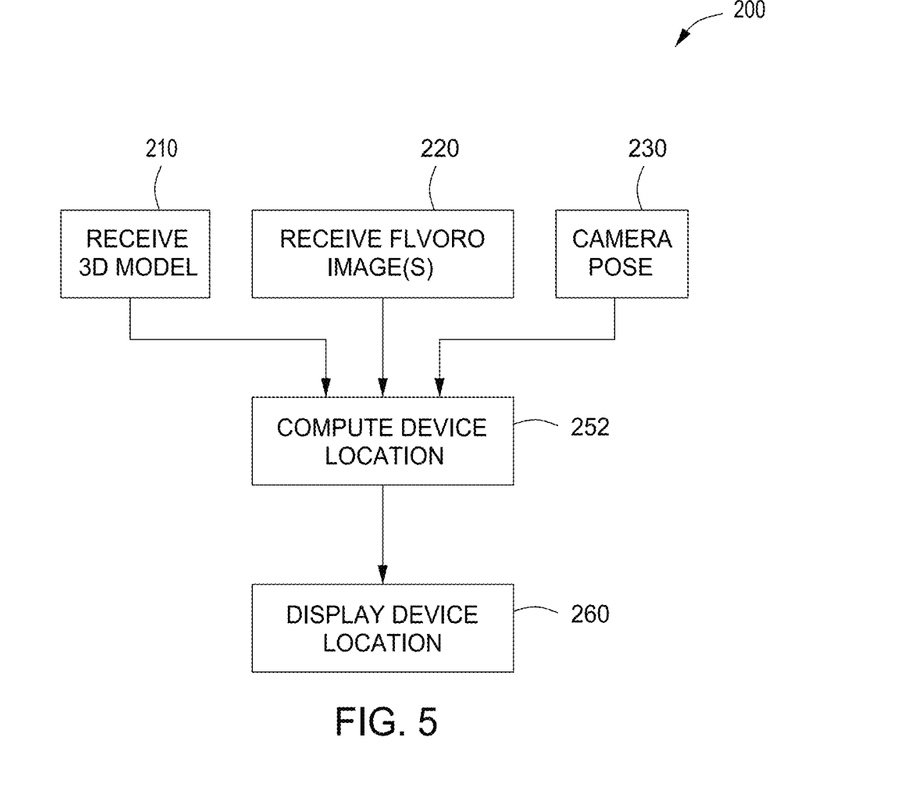
FIG. 5 is a flow chart of a surgical procedure for tracking a surgical device in a body organ during a live procedure.

FIG. 5 is flow chart diagram illustrating a surgical device tracking method 200 in accordance with one embodiment of the present invention for assisting a physician track a surgical device during a live procedure. The steps may be carried out on a computer or system and include: step 210 receiving 3D model information about a body organ of the subject; step 220 receiving at least one real-time fluoroscopy image of the body organ, step 230 receiving a real time camera pose of the fluoroscopy camera; step 252 computing the 3D location of the surgical device in real time; and step 260 displaying the surgical device location.

The step 122 of creating a 3D model of a body organ, in one embodiment, includes creating a 3D model of a non-rigid body organ such as the lung in a first body position or first patient position. The 3D model of the body organ is created from input including available image data from the subject patient such as high resolution computed tomography (HRCT) scans. An exemplary technique to determine a 3D model of the body organ is disclosed in U.S. Pat. No. 7,756, 316 entitled "Method and system for automatic lung segmentation". See also, U.S. Pat. Nos. 7,889,905 and 7,756,563; and Patent Publication No. 2008/0183073 all to Higgins et al.

Step 220 recites receiving fluoroscopy images of the patient. These are real-time fluoroscopy images of the body organ as described above in connection with FIG. 4.

Step 230 recites fluoroscopic camera pose. The real time camera pose (e.g., a 2D X-RAY unit, C-ARM, or fluoroscope camera) is an input to step 252 described more below. Camera pose may be obtained variously including, for example, with an external sensor, such as the Polaris Spectra tracker manufactured by NDI in Waterloo, Ontario, Canada. The position of fluoroscope camera is initially recorded and the fluoroscope image is initially registered with an image of the 3D model. The initial registration may be performed based on a rigid anatomical feature or another mark that is in a known location. The initial camera pose is recorded. As the fluoroscope camera is moved, the external camera sensor monitors the position and the pose is updated from the initial pose. In this manner, a real time camera pose may be input into the computation step 252. It is to be understood that the above camera pose step is only one approach to providing camera pose. Other techniques may be employed to provide a continuous camera pose and including without limitation optical, electrical, or software based approaches to monitor the position of the fluoroscopy camera, and determine its instant real time pose.

Step 252 computes the 3D location of the device in the model of the body organ. A number of approaches may be utilized to carry out this step.

In one embodiment of the present invention, step 252 identifies a reference mark in the fluoroscopy image received from step 220. The reference mark may vary widely and have a shape as, for example, a cross, ring, pattern of spots, etc. The reference mark is visible under fluoroscopy and, preferably, present on the surgical device.

A non-limiting example of a reference mark is a cross having four legs. Each leg has a different length. The cross may be present on the end of a catheter. By observing the dimensions of the reference mark, and the other inputs, the location and orientation of the surgical device may be computed. An exemplary technique or algorithm to compute the location of the mark based on the reference mark is normalized cross correlation template matching, which translates and rotates a small image patch with similar appearance as the reference mark in terms of grayscale values and scaling and compares the patch with a subset of the image under consideration. This approach is well-known in the art and is described, for instance, in the textbook Digital Image Processing by Gonzalez and Woods. After correcting for differences in the mean intensity level and variance in both the patch and the sub-image region under consideration the correlation between the two can be determined. Regions with high correlation indicate the presence of the reference mark. Once the reference mark is identified in 2D fluoroscopic image, its 3D pose can be estimated using 3D-2D pose estimation algorithm. One such algorithm is given in Reference 1, listed below.

In another embodiment of the present invention, step 252 includes computing the 3D location of the surgical device based on certain constraints or assumptions about the location of the surgical device. In particular, an embodiment of the present invention computes the 3D location of the surgical device based on the constraint that the surgical device is within an airway of the lung. With this assumption, the real time fluoroscopy image may be matched with a model image using an approach similar to that described above, such as normalized cross-correlation. In this embodiment, however, the sub-image locations over which the maximum normalized-cross correlation value is found is limited to the binary region in the fluoroscopic image where an airway tree-segmentation is projected. In this way, the search space for the reference mark is limited to where the airways may be located and precludes, for instance, the heart, parenchyma and ribs. To carry out 3D-2D registration, matching of the images may be performed using one or more fluoroscopy images.

In another embodiment of the present invention, step 252 includes computing the 3D location of the surgical device based on a plurality of fluoroscopy images and in particular, based on determining an intersection of a ray extending from the fluoroscopy unit, to the reference mark of the device in each of the plurality of fluoroscopy images. Since the fluoroscopic camera pose is known for each fluoroscopic image, the 2D reference mark is associated with a 3D ray from the camera. Calculating the rays and corresponding intersection of the rays from multiple images is described in D. A. Forsyth and Jean Ponce, "Computer Vision: A modern approach", Prentice Hall Professional Technical Reference, 2002.

Step 260 recites displaying the surgical device location. A number of views and images may be sent to a display as described above in connection with step 150 of FIG. 3.

In another embodiment, a method and system compute a 3D location of the surgical device based on registering the 3D model of the body lumen with video images from an endoscope for a portion of the surgical procedure and compute a 3D location of the surgical device based on registering the 3D model of the body lumen with fluoro images for another portion of the surgical procedure. In this manner, fluoroscopy is not required to track a device while the device is within the luminal structures such as the airways. The fluoroscope may be turned off. This is desirable.

Once the surgical device is to be advanced or placed outside of the airway, fluoroscopy-based tracking may be carried out in accordance with one of the embodiments of the present invention disclosed herein. As noted above, the position of the device in the airway tree may provide additional or confirmatory device position or orientation information as the device leaves the airway tree and begins to move through lung tissue.

In another embodiment of the invention, a method computes a candidate fluoroscope pose to place the fluoroscope component during a surgical procedure. The candidate pose or suggested pose serves to optimize visibility of a surgical device in the body organ of the subject during a procedure. The surgical device may vary widely and include, for example, catheters, and other cylindrical or tunnel-like structures.

In one embodiment of the invention the method for estimating a candidate fluoroscopic pose includes: a) receiving a candidate device pose of the surgical device within the body organ of the subject; and b) automatically computing at least one fluoroscope camera pose based on a feature of the surgical device visible under fluoroscopy, the position of the subject, and mechanical properties of the fluoroscope.

The receiving step may include receiving various information about where the surgical device shall be placed within the body organ during the procedure. For example, the physician may specify coordinates in a 3D model of the lung where a surgical device shall be positioned. The information may also be provided from a surgical planning module or workstation adapted to identify surgical plans. Planning information may include pre-guidance knowledge of the planned location and orientation of the surgical device. Such planning information may include fusing the surgical device with segmented anatomical structures and/or the CT data set. A description of a planning system and method is disclosed in U.S Patent Publication No. Patent Publication No. 2008/0183073 to Higgins et al. Additionally, an example of a commercially available planning workstation is LUNGPOINT® Virtual Bronchoscopic Navigation System, manufactured by Broncus Technologies, Inc. (Mountain View, Calif.).

Next, the method or system automatically computes at least one fluoroscope camera pose based on: a) a feature of the surgical device visible under fluoroscopy, b) the position of the subject, and c) mechanical properties of the fluoroscope.

Features of the surgical device include size, length, width, thickness, and other parameters such as without limitation symbols and indicia which may be present on the device and visible under fluoroscopy. These features are useful to optimize the fluoroscopic pose of the device. In one embodiment the computation step is carried out so that the length of surgical device appears as long as possible throughout the rotation of the C-arm along an arc. The arc can be depicted using visual cues.

Visual cues can depict in external movement of the C-arm along an arc in space by drawing the arc in 3D, or by generating virtual fluoroscopic renderings along said arc. To determine the arc, the arc that maintains the elongation of the device throughout all vantage points is one in which the cylindrical object running direction is normal to the plane in which the C-arm swings. The origin of the plane, and the center of rotation for the arc, is at the center of the location of the device object.

The position of the subject and mechanical properties of the fluoroscope are also inputs in the above referenced computation step. Indeed, the C arm cannot give any arbitrary view that a virtual fluoro image can, as, e.g., the patient cannot fit into the C arm opening from all vantage points. In one case (e.g., trying to image the patient from head to toe), patients are much taller than the opening of the C-arm and it is therefore impossible for the C-arm to reach such views. This so-called "no go" region for the fluoroscope can be estimated using knowledge of the width of the patient (discernable from the CT scan), clearance below the bed on which they lie in the surgical suite and any other obstacles that may be present. Once the orientation of the patient is known in CT, the top to bottom dimensions of the patient can be extended, mathematically, infinitely, creating an infinitely long "box" in which the fluoroscope emitter or detector cannot enter. With knowledge of this box, and the desired minimum arc length/angular rotational displacement of the fluoro views between vantage points, an optimization problem can be constructed to find an arc that satisfies the requirements of maximizing the projected length of the device in projected views while not entering the "no-go" region where the fluoroscope does not fit.

The users may pick from a handful of pre-set orientations that are familiar to them, such as an Anterior Posterior (AP), Left, Right, etc. In this embodiment, the pre-defined orientations are enumerated and a subset of a given range, described below, could be chosen such that the subset maximizes the projected length in the subset of views when compared to other views.

As an example of such subsets, there are typically at least two principal directions in which the C-arm can be easily be rotated, specifically the cranial/caudal arc and the left/right arc. The approximate center of rotation for these is at a point midway between the x-ray source and detector, the total distance of which is given by $d_{SD}$. The value $d_{SD}$ is on the order of one meter in separation. The entire C-arm unit can be translated on the floor so that the left/right arc of rotation swings around different portions of the patient. The plane in which the left/right arcs lie correspond to the anatomy depicted in a transverse CT slice. Likewise the plane in which the cranial/caudal rotates corresponds to a sagittal slice. Exemplary ranges of subsets include −60 to 60 degrees left/right in 5 degree increments as well as −45 to 45 cranium/caudal in 5 deg increments with both deviations measured from AP.

In one embodiment, to optimize viewing directions of a surgical device (for example, a straight tunnel like object in this instance) within the body, the object is modeled as a three-dimensional line segment whose endpoints are given by $P_1=\{x_1, y_1, z_1\}$ and $P_2=\{x_2, y_2, z_2\}$ in the CT coordinate system, measured in mm. While this example is directed to a simple straight object, any object whose geometry can be parameterized could be used instead.

The center of rotation of the C-arm unit, with respect to the CT coordinate system attached to the patient is given by $C_T=\{w_{CT}/2, h_{CT}/2, z_T\}$ where $w_{CT}$ is the total width of the CT scan in mm, $h_{CT}/2$ is the total height of the CT scan in mm, and $z_T=(z_1+z_2)/2$. This center of rotation quantitatively corresponds to the qualitative description presented in the previous paragraph. For a CT coordinate system where the x direction increases from right to left, y increases from anterior to posterior and z increases from head to toe, left/right rotation angle $\theta$ and cranial/caudal rotation $\phi$, typical camera (source) locations can be found in the cranial/caudal direction by $p_{cc}^a=C_T+\frac{1}{2}d_{s_p}\{0, \cos(\theta_a), \sin(\theta_a)\}$, $\phi_b=[-45°, 45°]$ (nominally) and the left/right by $p_{lr}^b=C_T+\frac{1}{2}d_{s_p}\{-\sin(\phi_b), \cos(\phi_b), 0\}$ with $\theta_a=[-60°, 60°]$ (nominally) and a and b acting as indexing integers. The locations of potential fluoroscopic imaging directions along either arc can be quantized into discrete angular displacements to match markings on the C-arm, for instance in 1-degree or 5-degree increments.

Figure 6:
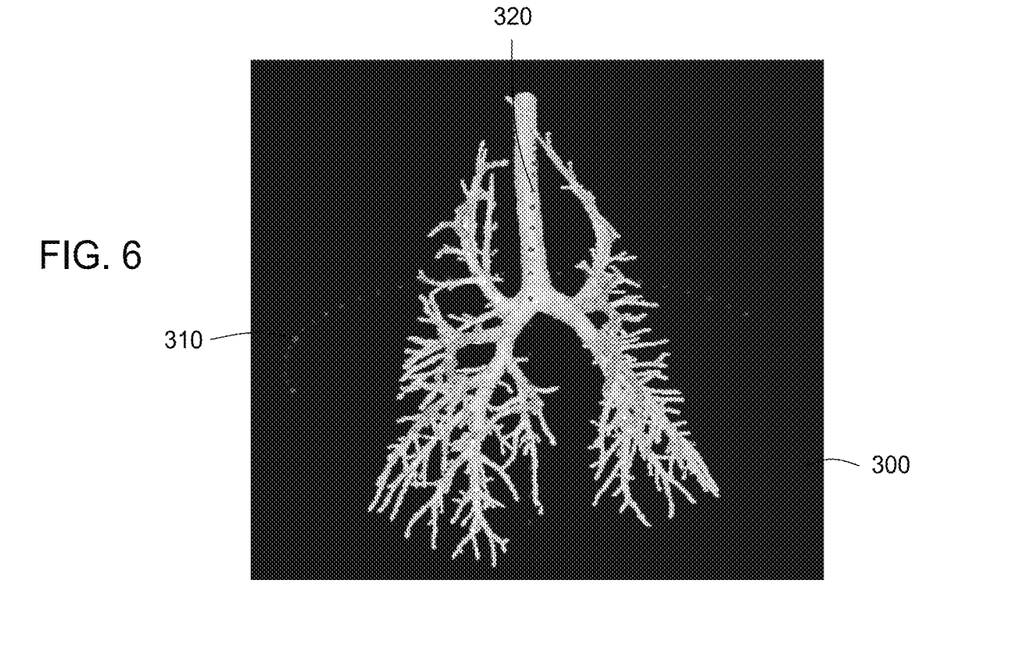
FIG. 6 is an illustration of a display of the airway tree and points indicating the location of a fluoroscope component.

An illustration of such a geometry is shown in FIG. 6, where the points 310 and points 320 indicate the left/right and coronal/caudal locations respectively of a detector above the patient. Note that the source (or camera, in typical vision parlance) is oriented 180 degrees from the detector below the patient; it is the detector whose position is noted by the radiologist.

With possible camera locations, the center of projection, and the endpoints of the device defined in the CT coordinate system, it is possible to define optimal camera locations for observing the end points of the device in the following manner. First define the viewing direction of the camera in the L/R arc as follows (the normal for the coronal/caudal is similarly defined):

$$n_{cc}^a = \frac{C_T - p_{c_c^a}}{\|C_T - p_{c_c^a}\|}$$

Next define two more unit vectors $u_{cc}^a$ and $r_{cc}^a$ such that $n_{cc}^a$, $u_{cc}^a$ and $r_{cc}^a$ are mutually orthonormal and therefore form an orthonormal basis.

Next, for each endpoint define its location in the a new coordinate system $$\text{by:} \begin{bmatrix} i_1 \\ j_1 \\ k_1 \end{bmatrix}_a = [u_{cc}^a \; r_{cc}^a \; n_{cc}^a][p_1 - p_{c_c^a}]$$

Where $[d_{cc}^a \; r_{cc}^a \; n_{cc}^a]$ is a 3×3 orthonormal matrix and the calculation for $p_2$ follows similarly. The perspective location for the endpoints in the 2D fluoroscopic image is therefore, $$p_1^{proj}{}_a = \begin{bmatrix} \frac{i_1}{k_1} & \frac{j_1}{k_1} \end{bmatrix}_a, \text{ with } p_2^{proj}{}_a$$

similarly defined. The 2D distance between the endpoints of the tunnel in a given fluoroscopic view is d2 $D^a = \|p_2^{proj}{}_a - p_1^{proj}{}_a\|$.

If we were interested in the single best view that gives the best view of the tunnel, then the optimization would be achieved by $$\operatorname*{argmax}_{a} d_{2D}^a.$$

However, since a single fluoroscopic view can be deceiving, the optimization requires finding a set of at least 2 optimal views. For sufficient separation, in a given arc these 2 views need to be separated by an angle of least a (nominally 30 degrees). An appropriate (although not the only) optimization function that ensures both views are large is to use the geometric mean, and optimize based on the following:

$$\operatorname*{argmax}_{m,n} \sqrt{d_{2D}^m d_{2D}^n}$$

such that $$|\theta_n - \theta\_m| \geq \alpha.$$

Figure 7:
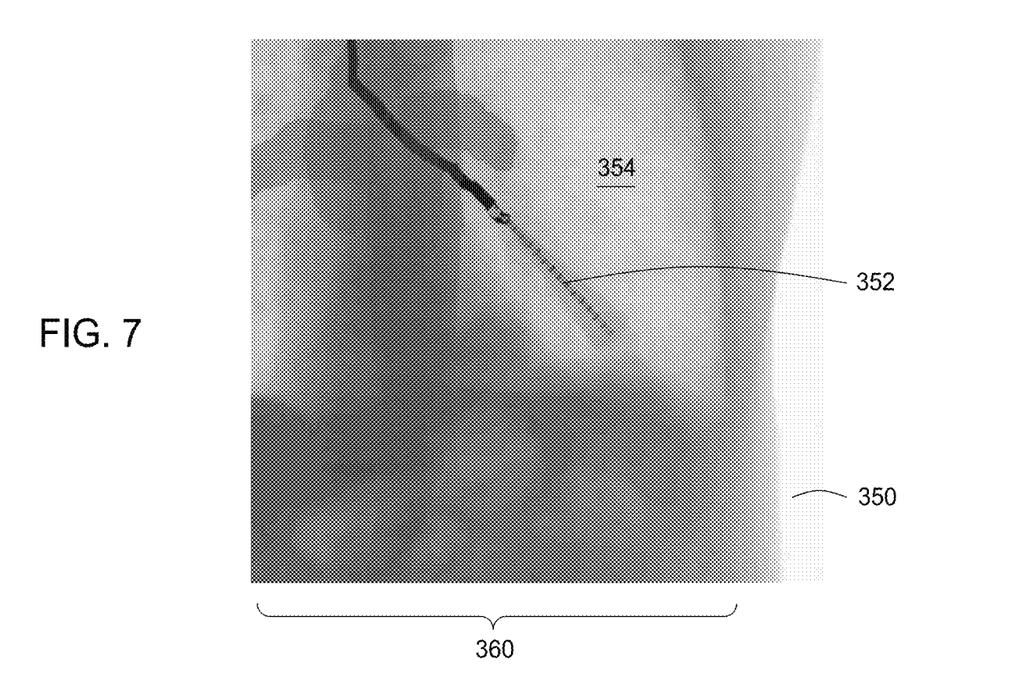
FIG. 7 is an illustration of a display of a 2D fluoroscopy image indicating a surgical device in an optimized view.

Combining this into a software system, a display 350 as shown in FIG. 7 may be provided to show the user where the detector should be placed to get optimal pair-wise projections in the different arcs for a given surgical device, and an image of the surgical device 352 in the body organ 354. In FIG. 7, instructions 360 are displayed.

Other modifications and variations can be made to the disclosed embodiments without departing from the subject invention.

We claim:

1. A method for tracking a surgical device in a body organ of a subject during a surgical procedure, wherein the body organ is a non-rigid body organ that changes shape as a result of varying patient body posture or position thereby defining an anatomy of unknown shape, the body organ comprising at least one body lumen, and said surgical device comprising a distal section having at least one reference mark which is visible under fluoroscopy, the method comprising the steps of:
   a) receiving a 3D image data set of the body organ and computing a 3D model of the body organ;
   b) performing a pre-tracking registration prior to tracking the surgical device during the surgical procedure thereby registering an image derived from the 3D model of the body organ with a real-time fluoroscopy image; wherein the pre-tracking registration comprises the following steps:
      receiving a pre-tracking position from a sensor indicating the position of a fluoroscopy unit;
      receiving a pre-tracking fluoroscopy image corresponding to the pre-tracking position;
      registering the pre-tracking fluoroscopy image with a pre-tracking image derived from the 3D model of the body organ; and
      recording the pre-tracking position;
   c) advancing the distal section of the surgical device outside of the at least one body lumen and into the anatomy of unknown shape;
   d) receiving a real-time fluoroscopy image showing the reference mark of the surgical device outside of the at least one body lumen and in the anatomy of unknown shape; and
   e) computing a 3D location of the surgical device in the 3D model based on a shape or pattern of the reference mark outside the at least one body lumen and within the anatomy of unknown shape and visible in the fluoroscopy image of step (d).

2. The method of claim 1 further comprising sending to a display the 3D location of the surgical device for displaying the 3D location of the surgical device in the 3D model of the body organ.

3. The method of claim 1 wherein the pre-tracking registration is determined based on identifying physical features of at least one of an anatomical feature and the surgical device.

4. The method of claim 3 wherein the pre-tracking registration is determined based on identifying anatomical features.

5. The method of claim 4 wherein the pre-tracking registration is determined based on identifying a spine.

6. The method of claim 4 wherein the pre-tracking registration is determined based on identifying one or more ribs.

7. The method of claim 1 wherein the pre-tracking registration is based on the surgical device being placed at a known location in the body organ.

8. The method of claim 7 wherein the pre-tracking registration is determined by minimizing the difference between a projected device location from the pre-tracking image and an actual device location shown in the pre-tracking fluoroscopy image.

9. The method of claim 1 wherein the step of receiving a 3D image data set of the body organ and computing a 3D model of the body organ comprises receiving a 3D image data set of the lung and computing a 3D model of the lung.

10. The method of claim 9 wherein computing a 3D model of the lung comprises computing a 3D model of a plurality of airways.

11. The method of claim 10 wherein the computing step is performed by a programmed processor.

12. The method of claim 1 comprising selecting the surgical device from the group consisting of a bronchoscope, interventional guide-sheath, needle, and probe.

13. The method of claim 12 wherein the selecting comprises selecting a surgical device based on the reference mark comprising a non-symmetrical pattern.

14. The method of claim 1 wherein the computing step is based on identifying the reference mark having a non-symmetrical shape.

15. The method of claim 14 further comprising determining the orientation of the surgical device based on the characteristics of the mark shown in the real-time fluoroscopy image.

16. The method of claim 1 wherein the computing step is based on identifying the reference mark comprising a first line segment and a second line segment perpendicular to the first line segment.

17. The method of claim 16 wherein the computing step is based on identifying the reference mark defining four arm segments and each of the segments having a different length.

18. The method of claim 1 wherein the step of receiving a real-time fluoroscopy image from a fluoroscopy unit comprises receiving only one fluoroscopy image showing the reference mark of the surgical device at the tracking location prior to moving.

19. The method of claim 1 comprising moving the surgical device, and repeating steps d) to e) subsequent to the surgical device being moved.

20. The method of claim 1 wherein the step of registering is based on monitoring the position of the fluoroscopy unit.

21. The method of claim 20 wherein the monitoring is carried out by observing a mark present on the fluoroscopy unit.

22. The method of claim 21 wherein the monitoring is carried out by observing a cross shaped mark.

23. The method of claim 1 wherein the step of computing the 3D location of the surgical device includes determining the orientation of the surgical device.

24. The method of claim 1 wherein the computing step is based on identifying the reference mark comprising a pattern.

25. The method of claim 1 further comprising deforming the 3D model of the body organ to match the body organ of the subject during the procedure prior to the registering step.

26. The method of claim 1 wherein the step of receiving a real-time image from the fluoroscopy unit comprises receiving a plurality of non-continuous discrete fluoroscopy images.

27. The method of claim 1 wherein computing the 3D location of the surgical device further comprises application of non-fluoroscopic constraints.

28. The method of claim 1 further comprising receiving a real-time endoscopic image of an airway and registering the real-time endoscopic image with the 3D model of the organ.

29. The method of claim 1 wherein the recording the pre-tracking position step is performed after the step of registering the pre-tracking fluoroscopy image.

* * * * *